United States Patent [19]

Schurig et al.

[11] Patent Number: 5,092,835

[45] Date of Patent: Mar. 3, 1992

[54] BRAIN AND NERVE HEALING POWER APPARATUS AND METHOD

[76] Inventors: Janet L. S. Schurig; Alma K. Schurig, both of 870 E. Walnut Ave., Provo, Utah 84604

[21] Appl. No.: 549,055

[22] Filed: Jul. 6, 1990

[51] Int. Cl.$^5$ ............................................. A61B 17/52
[52] U.S. Cl. .................................. 600/9; 600/15; 128/421
[58] Field of Search ............ 128/421, 422, 420.5, 128/420.6, 419 R; 600/15, 9, 12

[56] References Cited

U.S. PATENT DOCUMENTS

| | | | |
|---|---|---|---|
| 2,597,601 | 8/1948 | Sherman | 600/15 |
| 4,140,133 | 2/1979 | Kastrubin et al. | 128/421 |
| 4,524,773 | 6/1985 | Fischell et al. | 128/421 |
| 4,549,532 | 10/1985 | Baevmann | 600/15 |
| 4,776,322 | 10/1988 | Hough et al. | 128/420.6 |
| 4,940,453 | 7/1990 | Cadwell | 600/15 |

FOREIGN PATENT DOCUMENTS 2575926  7/1986  France ........................ 600/15

Primary Examiner—Francis Jaworski
Assistant Examiner—George Manuel

[57] ABSTRACT

An apparatus and method is provided for supplying healing power to the brain and nervous system which includes 1) applying a constant magnetic field in a cap or strap arrangement to the head or nervous system of a subject and 2) stimulating the nerves with electric signals applied to neural pathways to the brain located in the hands, feet and other parts of the body, with a view to A) aiding individuals suffering from nervous system disorders including i) serious disorders such as pervasive developmental disorder, autism, disorders caused by hypoxia, trauma and drugs, and some forms of schizophrenia, and also ii) mild disorders such as learning disabilities, and also B) heightening the mental and physical abilities of "normal" people.

22 Claims, 2 Drawing Sheets

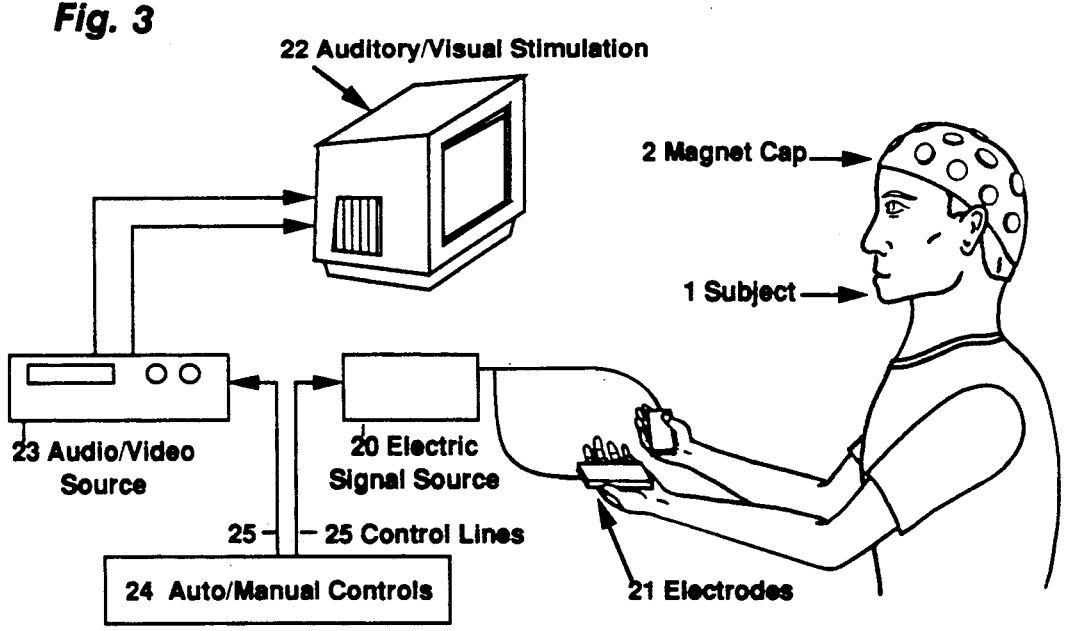

BRAIN AND NERVE HEALING POWER APPARATUS AND METHOD

FIELD OF THE INVENTION

This invention relates to the simultaneous therapeutic applications of a constant or static magnetic field to the human brain (or nervous system) in combination with the application of electric pulses to the nervous system in the hands, feet, head or other parts of the body, for the purpose of stimulating operation and repair of damaged or inactive nerve cells.

BACKGROUND OF THE INVENTION

Certain types of neurological disorders (particularly in young children) are diagnosed as Pervasive Developmental Disorder or Autism, for which the cause is undetermined (or linked to sedative induced hypoxia, drowning or drug impairment) and for which no successful treatment is available leading to recovery. Symptoms may include speech impairment, central auditory processing disorder, central vision loss, perceptual motor impairment and other neurological and behavioral disorders including schizophrenia. Often EEG's or MRI scans do not show major macroscopic damage, indicating that the disorder is microscopic and pervasive in nature—in which some percentage of brain cells in associated functional areas of the brain are inactive, and/or neurotransmission is impaired.

New instruments have been developed to study brain waves (See U.S. Pat. No. 4,736,751) by which it has been demonstrated by magnetoencephalograph that both electric and magnetic fields are generated by portions of the brain engaged in neurological activity. Magnetic fields arise both from individual axon and synapse transmission as well as from mass neuroelectric and neuro magnetic phenomena associated with processing stimuli and reacting thereto. Research in applying the instant method has shown that neurological phenomena produce an average constant or static magnetic field component of which the south pole is directed out of the head and the north pole inward.

The theoretical basis for the operation of the brain involves many phenomena besides individual and mass neuron interactions, including intra- and intercellular photon interaction and brain wave (electric, magnetic and electromagnetic) interactions, which is why brain and nervous system operation remains a subject of major research. Therefore, it is sufficient for the purposes of this invention to say that experiments indicate that when the naturally occurring magnetic field is reinforced with an external magnetic field, inactive nerve cells can be reactivated by electrical stimuli, such that inactive nerve cells or synapses become activated and lost or impaired neurological functions are restored or heightened. Sensory stimuli are beneficial but not necessary to the method.

Nerve impulse transmission parameters have been known for many years. Electrotherapy texts (such as Arthur L. Watkins' *A Manual of Electrotherapy*, Philadelphia, Lea and Febiger, 1958) provide the following nerve transmission parameters: 1) pulsed D.C.; 2) pulse duration—0.5 to 5 mSec.; 3) pulse frequency—20 to 80 Hz; and 4) maximum electrode current density—0.5 to 1.0 mA/sq.in. Numerous prior art commercial apparati have been designed to provide variations on the electrotherapy theme, most of which are designed to stimulate muscles and require current densities which are too strong for the present application. Electro acupuncture techniques (such as that described in U.S. Pat. No. 4,556,064) presume to stimulate or block nerve centers associated with specific acupuncture centers and their respective parts of the body, but no mechanism is provided for stimulating repair of pervasive brain damage.

Additional prior art techniques for stimulating the brain with electrical pulses (U.S. Pat. No. 4,646,744) or pulsed electric fields (U.S. Pat. No. 4,846,178) have been attempted; but in all cases the stimulation only involves electric stimulation. No magnetic field stimulation is proposed.

Magnetic fields have also been used without electric fields to stimulate biological tissues, both constant or static (U.S. Pat. No. 4,587,951) and dynamic (U.S. Pat. No. 4,693,238), but in all cases the stimulation has not involved application of a static magnetic field to the head or brain of a subject for the purpose of neurological healing and stimulation. In all cases, the electrical and sensory stimulation would be lacking.

Electromagnetic fields have been proposed, (U.S. Pat. No. 4,683,873) but an electromagnetic field is different in its effect than electric pulses. Care must be taken to differentiate between the "magnetic" field produced by 1) an "electromagnet" operated in a DC current mode (i.e., electromagnet magnetic field), 2) the electromagnetic field produced by an AC excited electromagnet in which an electromagnetic wave or radio wave is produced, and 3) the noninterruptible magnetic field characteristic of a permanent magnet. The third type is required by the herein specified method.

An electromedical device (U.S. Pat. No. 4,838,850) has been proposed which uses both alternating magnetic and alternating electric fields to excite circular motion of ionic species in the blood and cells, creating the effect of increased circulation in body tissues. The alternating or time-varying magnetic field is not the type found effective in the herein described apparatus and method.

No prior art electrical, magnetic or electromagnetic technique employs 1) a constant magnetic field to reinforce naturally produced neuro-magnetic fields and 2) electrical stimulation through neural pathways at neural frequencies to activate inactive synapses and assist the brain and nervous system in restoring neurological functions.

The electric and magnetic stimuli alone are sufficient to increase neurological functions, although simultaneous sensory stimulion is beneficial.

OBJECTS OF THE INVENTION

Accordingly, it is an object of the present invention to provide an effective method of brain and nervous system therapy with a static magnetic field applied to the brain or nervous system, and with electric signals applied at those parts of the body with the required neural pathways to the affected part of the brain and nervous system.

It is a further object to provide a therapeutic method of treating neurological disorders by applying a static magnetic field of proper polarity to the brain and by applying electric signals and sensory stimuli to the nervous system which act to stimulate affected areas of the brain.

It is a further object to provide neurological system therapy by means of a cap or hat to which permanent magnets may be affixed in the proper zones, and by means of a relatively simple-to-operate electric signal generator which has been programmed for the patient's requirements and can be operated safely at home or in a clinical setting.

An additional object is to provide a method and system (for treating neurological disorders) consisting of 1) means for modifying the shape and intensity of the static magnetic field applied to the affected part of the neurological system by using an array of magnets affixed to a hat or clothing arrangement; 2) means for providing and controlling audio/visual and other sensory stimuli; 3) means for providing and controlling all parameters of electrical signals applied to neural pathways at different parts of the body sequentially or simultaneously, including the hands, feet, ears, head and other locations; and 4) means for coordinating and synchronizing all sources of stimuli under computer or manual control so that neurobiological synergism is enhanced and maximum individual neurological function is enhanced.

These and other objects and advantages of the invention and method will become more fully apparent as the description which follows is read in conjunction with the drawings.

Description of the Invention

BRIEF DESCRIPTION OF THE DRAWINGS

FIG. 3 is an illustration of a system for providing neurological therapy comprising a magnetic hat, electric and audio/visual stimulation means and automatic/manual controls for all parameters.

DESCRIPTION OF THE PREFERRED EMBODIMENTS

Figure 1:
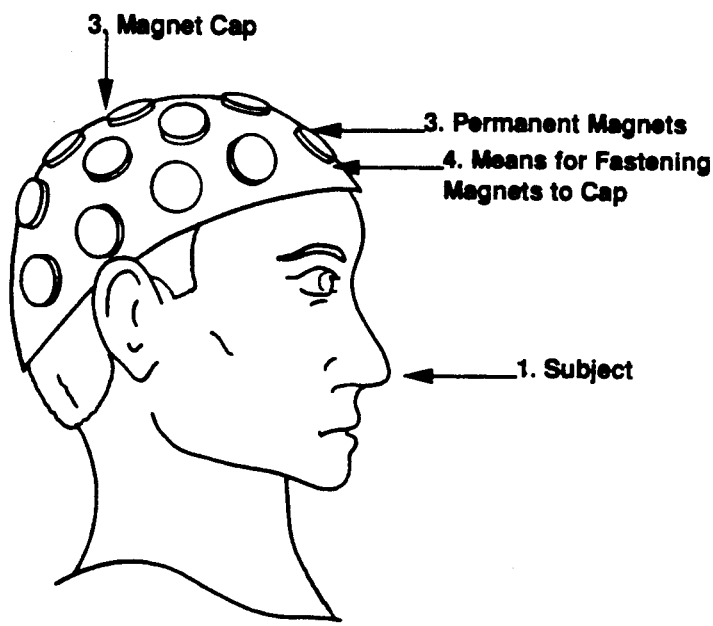
FIG. 1 is an illustration of a permanent magnet hat utilizing 1" diameter ceramic type permanent magnets.

Reference is first made to the magnet hat for providing neurological therapy illustrated in FIG. 1. The head of subject 1 is fitted with a magnet cap 2. The body of the cap or hat, made of cloth, may be readily purchased in department stores. The magnets 3 may be permanent magnets. The permanent magnets 3 may be low cost ceramic magnets about 2.5 cm in diameter and 0.6 cm thick, and are attached to the inside (or outside) of the hat with permanent or adjustable means of attachment 4 so that the number and position of the magnets can be adjusted to direct a magnetic field through the brain.

In reference to polarity, FIG. 1 illustrates that the magnets are usually oriented to direct the north pole into the head, which is effective and which reinforces naturally produced magnetic fields. The number and distribution of the magnets may be sufficient to permeate the entire brain with a magnetic field. Alternately, flexible sheet type magnetic materials could be used; also custom molds within a common range of sizes could be employed to create head shaped homogeneous magnetic caps.

Other parts of the body including the neck and spinal cord may also be provided with a therapeutic magnetic field by placing permanent magnets along the spinal cord from the head to the tailbone, a shirt, a strip, or a harness being prepared to align the magnets in the desired zones. Electric signals of necessity, and vibratory or tactile stimuli if desired, can be applied at the feet or other neural pathways so that the nerves of the spinal cord may receive electric stimulation in the presence of the magnetic field which stimulates activation of traumatized and damaged spinal cord nerves. Treatment should be applied as soon as possible after damage.

Figure 2:
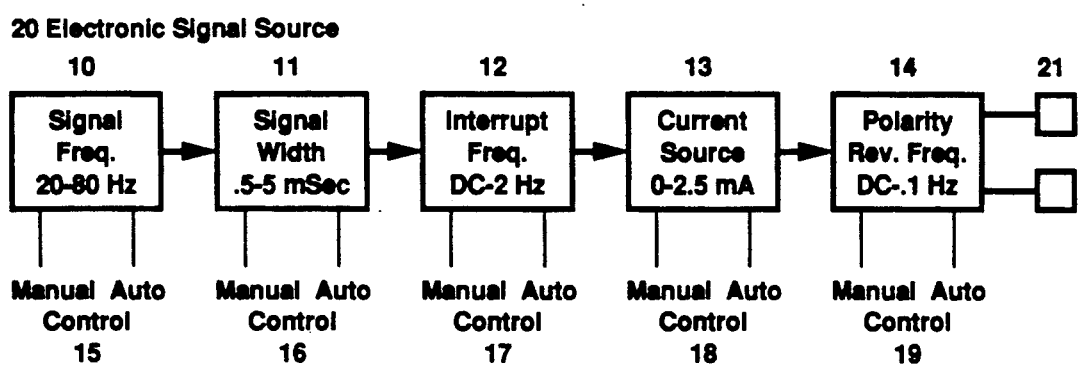
FIG. 2 is a functional block diagram of an electrical stimulation apparatus detailing the range of adjustment of most parameters.

FIG. 2 provides a block diagram of an electric signal source 20 for transmitting neural stimulation signals through the nervous system of a subject via electrodes 21. Subsystem 10 is an astable oscillator which can be manually or remotely adjustable by controls 15 to produce signal frequency range of 20 Hz to 80 Hz; this range includes the lower neural transmission band and is the range used naturally by the body. Frequencies higher than 100 Hz (but below 1 kHz) are considered to be blocking frequencies as opposed to stimulation frequencies and are not to be used. The 30 to 40 Hz range has been found to produce satisfactory results for the purpose of brain healing in conjunction with a static magnetic field. The output of signal frequency generator 10 triggers a monostable multivibrator signal width generator 11, the pulse width of which is adjustable between 0.5 to 5 mSec by manual or automatic controls 16. Pulse widths of 1 to 2 mSec are favored for neural signal transmission purposes, with 20–30 mSec off periods between signal pulses (30–50 Hz).

To reduce acclimation of the brain and nerves to the electrical stimulation, the nominal 35 Hz signal frequency at 11 may be interrupted at low frequency (DC to 2 hz) by an astable frequency generator 12, the frequency of which is adjusted by manual and automatic controls 17. The periodically interrupted signal train output of 12 then drives a pulsed current source 13 which converts the voltage pulses to current pulses of 0 to 2.5 mA peak, the amplitude of which is adjusted by manual and auto controls 18. The conversion from low voltage pulses to current pulses accommodates variations in skin resistance, electrode contact resistance and nerve conductivity between different individuals. The output circuit of the current source has been provided with an autobiasing circuit to keep the integral of the output current zero to avoid electrochemical reactions between the skin and electrodes. But, this is not essential to the operation of the method. A further circuit for increasing the bilateral stimulation of the brain and for reducing acclimation of the brain and nerves to the signals is an output circuit which has been provided with a polarity reversal oscillator 14 and switch with manual and auto controls 19 for adjusting the rate of reversals from DC to 0.1 Hz (10 seconds or longer per reversal).

The actual circuitry for providing the basic astable and monostable circuits 10 through 12 and 14 may be provided by circuitry as simple as a single 74C14 hex schmidt trigger with attendant RC time constants. The current source 13 is an NPN signal transistor configured as a current source and biased appropriately. The polarity reversal switch is a DPDT low power relay. The power supply may be 1) either a wall socket transformer or a battery with a converter circuit, to supply 30 volts for the current source and 2) a readily available low power 5 or 8 volt regulator for the 74C14, which is a low power CMOS device.

The manual controls 15 through 19 consist of potentiometers, some with lockable shafts so that operating parameters (such as maximum signal current) may be set for a specific individual and treatment regimen. The automatic control counterparts 15–19 consist of CMOS multiplexers (such as the CD4066) which select fixed resistances of binary or logarithmic weighting, as required, to allow selection of the desired parameters by computer interface ports (such as 8,255 or 74,574 chips).

For electrodes 21 any commercial electrode may be used with a surface area of 10 sq.cm to 25 sq.cm. Common materials vary from standard carbon impregnated polymers to stainless steel plates covered with moistened conduction pads. Thin layers of flexible conductive polymer material could be woven into gloves, such that multiple sets of electrodes could be provided in each, making contact with the desired neural pathways to the brain. The gloves could be provided with ties to keep them on the hands of children during treatment, while current densities are always kept low enough to avoid pain, burning or discomfort. Different sets of electrodes corresponding to different neural pathways could be energized manually or automatically as part of a specific treatment procedure.

FIG. 3 illustrates a neurological therapy system consisting of a magnet cap 2 worn on the head of subject 1, who holds electric stimulation electrodes 21 in his hands while listening to and watching optional auditory/visual stimulation means 22. As stated herein, the sensory stimulation is beneficial but not necessary for improvement of brain cell activity. The audio/video source could be a HiFi VCR or laser disc player, or a live presentation. Certain commercial laser disc players have digital/computer interfaces so that specific sources can be selected by automatic controls 24. By means of control lines 25 to the audio/video source 23, electric signal source 20 and/or magnet hat 2, it is possible to synchronize by controls 24 auditory and/or visual stimulation with magnetic and electrical stimulation, which can be beneficial in some cases.

Many variations on the system illustrated in FIG. 3 are readily manifest from previous discussions herein. The magnet cap 2 can be made with permanent magnets. The areas of stimulation can include the spinal cord and other parts of the nervous system. The electrodes 21 can be placed on any part of the body with the desired neural pathways to the nerve or brain zones to be treated. Multiple electrodes 21 with single or duplicate electric signals sources 20 can be separately or simultaneously placed at various parts of the body, under manual or automatic control. The auditory/visual stimulation can be provided by a variety of media or none at all. The programmed entertainment and/or lessons can be directed at training those areas of neurological development needed by a subject, for instance, drawing the letters of the alphabet, reading words, hearing and speaking words, learning to recognize and differentiate colors, learning numbers and counting, etc. Perceptual motor and other neurological development patterning exercises as well as physical stimulation by shape, texture, and temperature and emotional support through sincere expressions of love can be beneficial in a program for complete treatment of and recovery from neurological damage, as required.

Automatic controls 24 can consist of a sophisticated computer program and data bank which not only controls the treatment procedures, but also tracks the history and development milestones of each subject. Feedback systems based upon appropriate test parameters could also be incorporated into the system.

By way of caution, while computer operation of all system controls may be convenient in a clinical setting, it does not eliminate the value of a knowledgable human operator who applies experience, intuition, common sense and love in his treatment of a rear and unique subject.

While the present invention has been described and illustrated in conjunction with a number of specific embodiments, those skilled in the art will appreciate that variations and modifications may be made without departing from the principles of the invention as herein illustrated, described and claimed.

Having thus described the invention, what is claimed is:

1. A system for providing stimulation energy for promoting healing in a neurologically impaired human brain of a subject comprising:
    means for applying a magnetic field of constant intensity to the brain of said subject, and
    means for applying electric stimulation signals in combination with said magnetic field to various parts of the body of said subject which have neural pathways to the brain of said subject for promoting healing of the neurological functions of the brain.

2. The system as set forth in claim 1 which further comprises:
    means for providing at least one of the following:
        A) sensory stimuli,
        B) neurological development therapies,
        C) physical education therapy, and
        D) mental education therapy,
        to said subject.

3. The system as set forth in claim 1 in which:
    said means for applying the magnetic field to the head of the subject comprises a head piece to which a plurality of magnets in the form of discrete units and straps of flexible permanent magnetic material are attached with the north pole of said magnets directed towards the head when the head piece is placed on the head, and
    said means for applying electric stimulation signals comprises means to produce a train of current pulses with a pulse repetition frequency of 20 to 80 Hz., a pulse width of 0.5 to 5.0 mSec, a pulse amplitude of 0 to 2.5 mA., and a pulse polarity selected from unipolar sources and bipolar sources with the integral of current flow equal to zero when averaged over a complete pulse cycle and capable of periodic polarity reversal, and
    said means for applying said electric stimulation signals further comprises a non-invasive electrode means having a surface area sufficient to keep the peak current density of said electric stimulation pulses below 1 mA/sq.in. when applied to said parts of said subject's body.

4. A method of stimulating the brain and nervous system of a subject comprising the steps of:
    applying a magnetic field of constant intensity to the brain of said subject, and
    applying stimulation signals to the brain through the nervous system of said subject.

5. A method as set forth in claim 4 wherein the magnetic field is provided by permanent magnets.

6. A method as set forth in claim 4 which includes the further step of:
    providing stimuli selected from the group consisting of:
        A) sensory stimuli,
        B) neurological development therapies,
        C) physical education therapy, and
        D) mental education therapy,
        for said subject.

7. A method as set forth in claim 4 wherein the step of applying electric stimulation signals further comprises:
applying an electric field to the nervous system of said subject.

8. A method as set forth in claim 4 wherein:
the magnetic field is unipolar,
the signals are current pulse trains with a pulse repetition frequency of 20 to 80 Hz., a pulse width of 0.5 to 5.0 mSec, a pulse amplitude of 0 to 2.5 mA., and a pulse polarity selected from unipolar and bipolar sources with the integral of current flow equal to zero when averaged over a complete pulse cycle, and
the electric stimulation signals are applied with the current density below 1 mA/sq.in. and said signals are applied through multiple neural pathways from multiple electrodes and electric stimulation sources by means selected from simultaneous and sequential sources.

9. A method as set forth in claim 4 including the further steps of:
monitoring, recording, coordinating and controlling at least one step including positioning locations for stimulation by means selected from magnetic, electric and sensory stimulation, so as to optimize parameters producing the greatest rate of improvement in said subject.

10. A method as set forth in claim 4 further comprising the steps of:
providing mobile and automatic stimulation sources such as magnetic, electric and sensory, to permit application of a neurological stimulation regimen over an extended period of time.

11. A method of stimulating the brain and nervous system of a subject comprising the steps of:
applying a magnetic field of constant intensity to the nervous system of said subject, and
providing stimuli selected from the group consisting of:
A) sensory stimuli,
B) neurological development therapies,
C) physical education therapy, and
D) mental education therapy,
for said subject.

12. A system for stimulating the brain of a subject comprising:
means for producing a magnetic field of constant intensity,
means for applying the magnetic field to the head of said subject, and
means for applying electrical stimulation signals in combination with said magnetic field to the brain of said subject.

13. The system as set forth in claim 12 further comprising:
means for providing neurological stimuli selected from the group consisting of:
A) sensory stimuli,
B) neurological development therapy,
C) physical education therapy, and
D) mental education therapy,
for said subject.

14. The system as set forth in claim 12 further comprising:
means for monitoring, recording, coordinating and controlling electric and magnetic stimulation parameters and physical areas of application of at least one stimulation means, so as to optimize the parameters of each stimulation means and increase the rate of neurological improvement in said subject, among other benefits.

15. The system as set forth in claim 12 further comprising:
means for assembling a plurality of permanent magnets selected from discrete and flexible magnetic sheet form, said magnets being incorporated into means for applying said magnets conveniently to desired parts of the head and nervous system of said subject.

16. The system as set forth in claim 12 in which said means for producing and applying the magnetic field further comprises means for assembling a plurality of magnets of any functional form into a head piece in a manner that permits the north pole of the magnetic field produced by said magnets to be directed towards the head of said subject when said head piece is placed on the head, said head piece permitting the number and location of said magnets to be either fixed or adjustable, as desired.

17. The system as set forth in claim 12 in which said electric stimulation signals are current pulse trains with a pulse repetition frequency of 20 to 80 Hz., a pulse width of 0.5 to 5.0 mSec, a pulse amplitude of 0 to 2.5 mA. and a pulse polarity which is selected from unipolar and bipolar sources with the integral of current flow equal to zero when averaged over a complete pulse cycle.

18. The system as set forth in claim 12 in which said magnetic and electric stimulation means further comprises
means for assembling a plurality of magnets of any functional form into a head piece in a manner that permits the north pole of the magnetic field produced by said magnets to be directed towards the head of said subject when said head piece is placed on the head and which permits the number and location of said magnets to be both fixed and adjustable, as desired;
means for producing current pulse trains with a pulse repetition frequency of 20 to 80 Hz., a pulse width of 0.5 to 5.0 mSec, a pulse amplitude of 0.0 to 2.5 mA. and a pulse polarity which is selected from unipolar and bipolar sources with the integral of current flow equal to zero when averaged over a complete pulse cycle, and
means for applying said electric stimulation pulses to the brain and nervous system of said subject through neural pathways to the brain located at various places of the subject's body by means of non-invasive means applied to said places of the subject's body, the electrode means having a surface area sufficient to keep the peak current density of said electric pulses below 1 mA/sq.in.

19. The system as set forth in claim 12 which further comprises:
means for permitting free physical mobility of said subject over extended time periods when undergoing therapy, such that said means for producing the magnetic field comprises permanent magnets, said means for applying the magnetic field to the head or nervous system comprises clothing structures which are conveniently and comfortably worn on the desired area of the head and nervous system, and
said means for providing electric stimulation signals is powered by means permitting physical mobility and comprises means for conveniently attaching and switching electric stimulation electrodes located at various parts of the body with corresponding nerve pathways to the brain.

20. A system for stimulating the brain and nervous system of a subject comprising:
    means for producing a magnetic field of constant intensity,
    means for applying said magnetic field to the head of said subject, and
    means for providing neurological stimuli in combination with said magnetic field selected from the group consisting of:
    A) sensory stimuli,
    B) neurological development therapy,
    C) physical education therapy, and
    D) mental education therapy,
    for said subject.

21. A method as set forth in claim 4 further comprising the step of:
    providing mobile and automatic stimulation sources such as magnetic, electric, and sensory, to permit application of a neurological stimulation regimen requiring substantial physical mobility.

22. A system for stimulating the nervous system of a subject comprising:
    means for producing a magnetic field of constant intensity,
    means for applying the magnetic field to the nervous system of said subject, and
    means for applying electrical stimulation signals to the nervous system of said subject.

* * * * *